United States Patent [19]

Choi

[11] Patent Number: 5,099,854
[45] Date of Patent: Mar. 31, 1992

[54] DIGITAL WRISTWATCH WITH THE FUNCTION OF A SPHYGMOMETER

[75] Inventor: Jong-oh Choi, Seoul, Rep. of Korea

[73] Assignee: Samsung Electronics Co., Ltd., Rep. of Korea

[21] Appl. No.: 494,759

[22] Filed: Mar. 16, 1990

[30] Foreign Application Priority Data

Mar. 18, 1989 [KR] Rep. of Korea .................. 89-3397

[51] Int. Cl.$^5$ ........................................... A61B 5/024
[52] U.S. Cl. ................................................. 128/690
[58] Field of Search ................ 128/666, 667, 689, 690

[56] References Cited

U.S. PATENT DOCUMENTS

| | | |
|---|---|---|
| 3,559,628 | 8/1971 | Abbenante . |
| 3,717,140 | 2/1973 | Greenwood . |
| 4,224,948 | 9/1980 | Cramer et al. ...................... 128/690 |
| 4,256,117 | 3/1981 | Perica et al. ........................ 128/690 |
| 4,331,154 | 5/1982 | Broadwater et al. ............... 128/690 |
| 4,406,290 | 9/1983 | Walbcoffe-Wilson et al. .... 128/690 |
| 4,450,843 | 5/1984 | Barney et al. ....................... 128/690 |
| 4,807,639 | 2/1989 | Shimizu et al. ..................... 128/690 |

Primary Examiner—Lee S. Cohen
Assistant Examiner—Krista M. Pfaffle
Attorney, Agent, or Firm—Morgan & Finnegan

[57] ABSTRACT

There is disclosed a digital wristwatch with the function of a sphygmometer comprising a sphygmus sensor for sensing the sphygmus numbers of a human body to convert them into electrical pulses, first counting circuitry for counting the electrical pulses outputted from the sphygmus sensor, first decoding and driving means for decoding the digital data outputted from the first counting circuitry to drive sphygmus numbers display, second counting circuitry for counting a predetermined time from the commencement of the pulse check mode, alarm means for generating alarm signal for a given time from the end of the predetermined time, and reset pulse generating means for resetting the first and second counting circuitries after the given time.

3 Claims, 4 Drawing Sheets

DIGITAL WRISTWATCH WITH THE FUNCTION OF A SPHYGMOMETER

BACKGROUND OF THE INVENTION

The present invention relates to a digital wristwatch with the function of a sphygmometer, whereby the user can easily make sphygmus measurement.

Rapid developments of electronic applied technologies and semiconductor chip manufacturing process, etc. have resulted in diversification and multi-functionallization of electronic equipment. For example, the digital wristwatch usually has additional functions such as informing the user of an appointment, memorizing phone numbers, performing mathematical calculations, etc. Moreover, as consideration to health care becomes more and more important, there has been suggestions for wrist watches digital wristwatch with the function of sphygmometer for measuring the user's sphygmus, such as the ones disclosed in U.S. Pat. No. 4,331,154, Japanese Patent No. sho 59-17189, etc.

However, the prior art digital wristwatch with the function of sphygmometer is based on operational calculus with a complicated circuit construction, such that it is difficult to lay out the circuit in one chip, resulting the an increase in chip size. Consequently, the production cost is also increased.

SUMMARY OF THE INVENTION

It is an object of the present invention to provide a digital wristwatch with the function of a sphygmometer, whose circuit construction is simplified and whose production cost is low.

It is another object of the present invention to provide a digital wristwatch with the function of a sphygmometer, which includes alarm means for announcing the ending of the pulse checking time.

According to the present invention, a digital wristwatch with the function of a sphygmometer comprises:

(a) a sphygmus sensor for sensing the sphygmus of a human body to convert them into electrical pulses;

(b) mode selecting means for selecting between the time record mode and the pulse check mode;

(c) first counting circuitry for counting the electrical pulses outputted from the sphygmus sensor when the pulse check mode is selected by the mode selecting means;

(d) first decoding and driving means for decoding the digital data derived from the first counting circuitry to drive sphygmus numbers display;

(e) second counting circuitry for counting a predetermined pulse time check when the pulse check mode is selected;

(f) alarm means for generating alarm signal for a of the predetermined time; and (g) reset pulse generating means for resetting the first and second counting circuitries after the given time.

BRIEF DESCRIPTION OF THE ATTACHED DRAWINGS

DETAILED DESCRIPTION OF THE PREFERRED EMBODIMENT

The present invention will now be described with reference to the drawings attached only by way of example.

Figure 1:
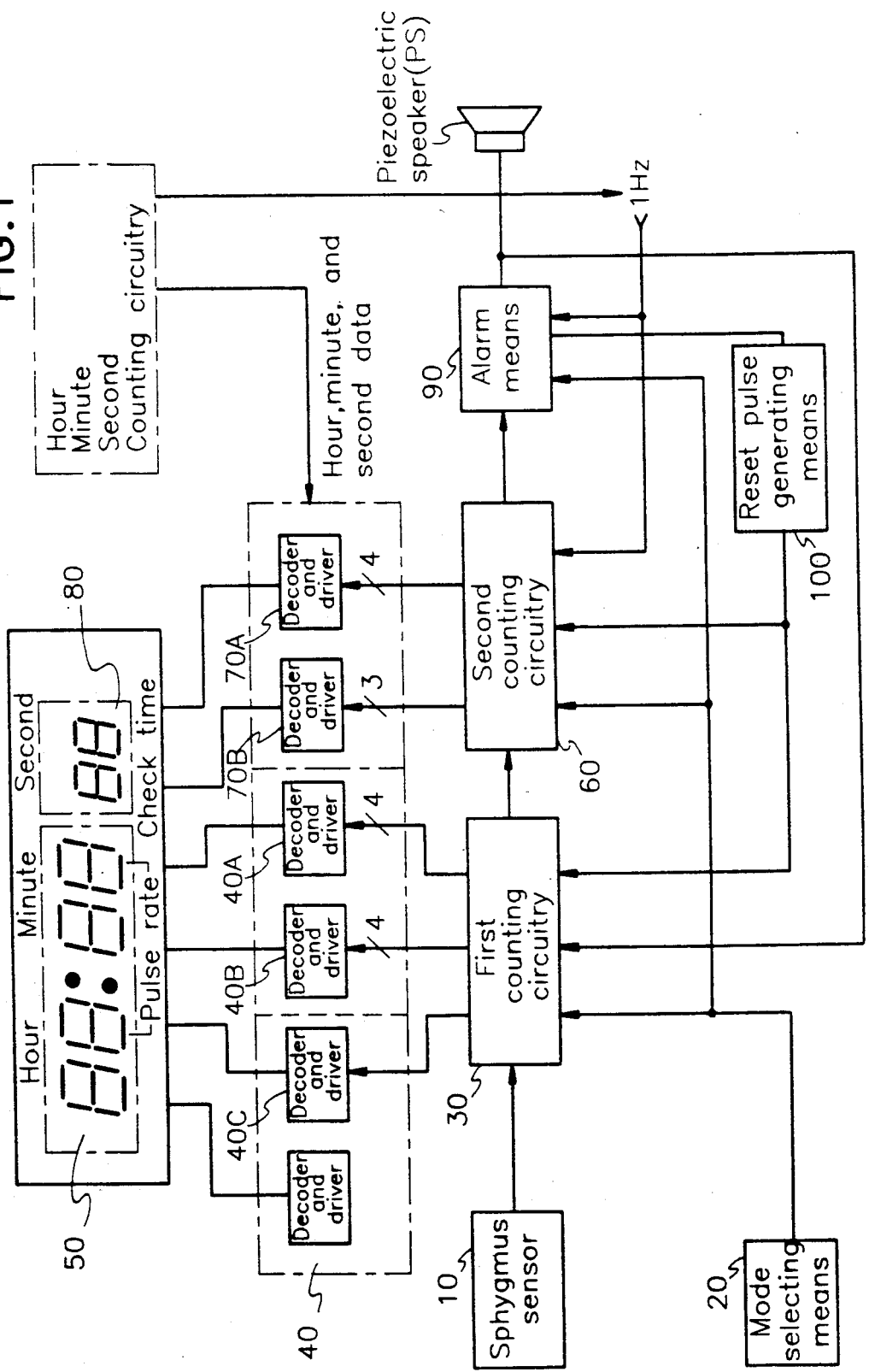
FIG. 1 is a block diagram of a digital wristwatch with the function of a sphygmometer according to the present invention.

Referring to FIG. 1, sphygmus sensor 10 is usually comprised of a piezoelectric sensor or photoelectric sensor, and converts the pulses of a human body into amplified electrical pulses. Mode selecting means 20 is to select between the time record mode and the pulse check mode to control first and second counting circuitries 30 and 60. First counting circuitry 30 counts the electrical pulses derived from the sphygmus sensor 10 when the pulse check mode is selected by the mode selecting means 20. The output of the first counting circuitry 30 is displayed on sphygmus numbers display 50 via a conventional first decoding and driving means 40. Second counting circuitry 60 counts 1 Hz pulses produced from a conventional time circuitry from the commencement of the pulse check mode. The second counting circuitry 60 counts down during a predetermined time, e.g. 60 seconds, whose output is displayed on pulse check time display 80 via a conventional second decoding and driving means 70. Here, the sphygmus numbers display 50 is the time/minute portion (four digits) of a conventional digital wristwatch, and the pulse check time display 80 is the second portion (two digits) thereof. Also, the second counting circuitry 60 generates a control signal to drive alarm means 90 after a predetermined time, i.e. 60 seconds. After receiving the control signal, the alarm means 90 delivers a control signal to the first counting circuitry 30 so that the first counting circuitry 30 stop receiving the electrical pulses from the sphygmus sensor 10. Hence, the first counting circuitry 30 counts the sphygmus numbers during the one minute interval until it is stopped, and the sphygmus numbers display 50 displays the counted pulses.

The alarm means 90 drives piezoelectric speaker PS to generate alarm upon receiving a control signal. Alarm means 90 also counts 1 Hz signal to generate an alarm signals for a given time, e.g., 20 seconds. Its thereafter drives reset pulse generating means 100 to reset the first and second counting circuitries 30 and 60. If the second counting circuitry 60 is reset, the control signal delivered to the alarm means 90 is stopped, the piezoelectric speaker PS no longer sounds the alarm, and the system returns to the initial state.

Figure 2:
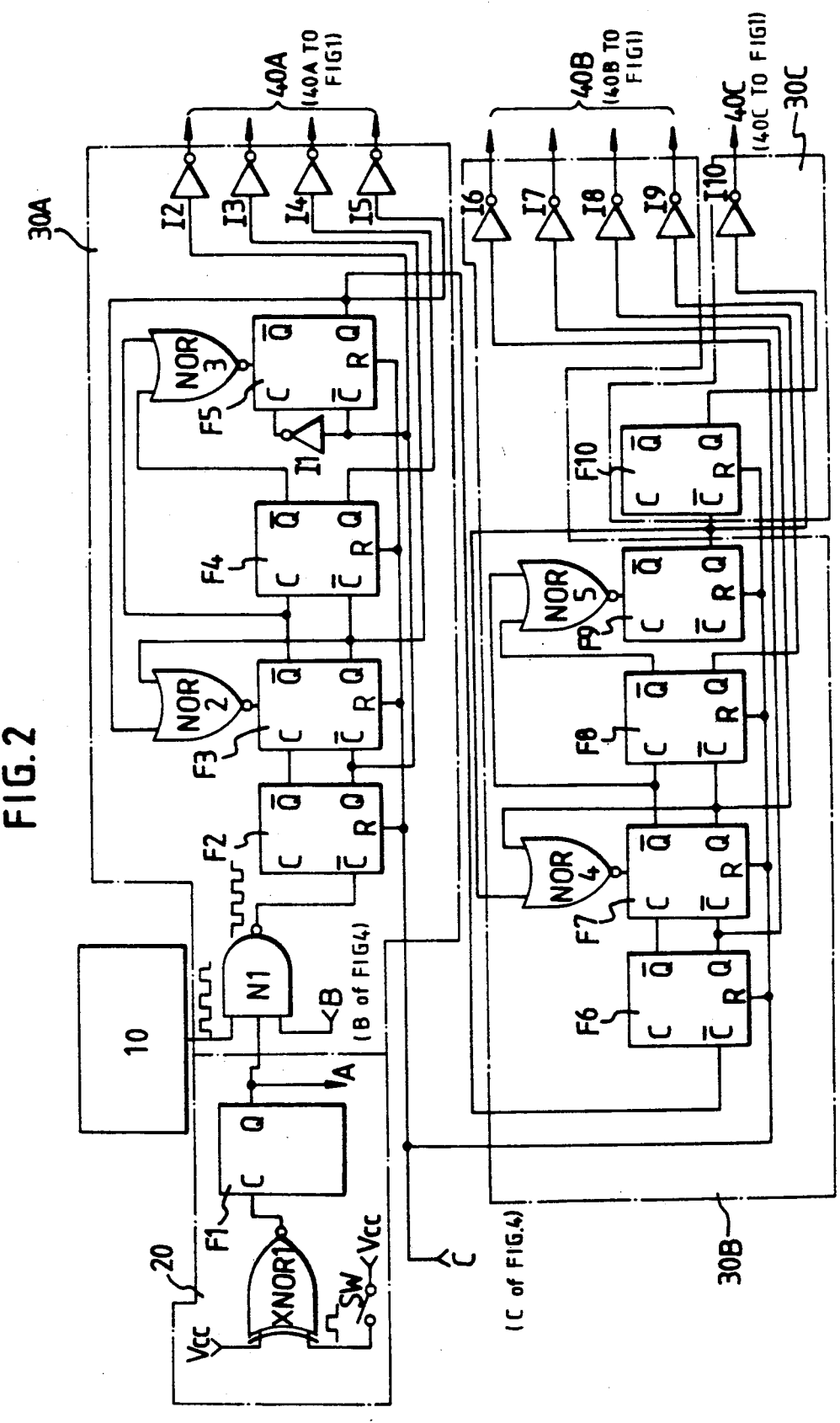
FIG. 2 is a detailed circuit diagram for illustrating mode selecting means and first counting circuitry of FIG. 1.

Referring to FIG. 2, the mode selecting means 20 comprise an exclusive NOR gate XNOR1, which reverses the operating signal of toggle switch SW supplied to the clock terminal C of flip-flop F1.

The first counting circuitry 30 comprises a NAND gate N1, which receives the output signal of flip-flop F1, the output signal of sphygmus sensor 10, and the output signal of AND gate AN13 in alarm means 90. The output signal of the NAND gate N1 is used as a clock pulse of the units digit counter 30A. The units digit counter 30A comprises a plurality of flip-flops F2, F3, F4 and F5, and inverters I2–I5. The output pulse of the sphygmus sensor 10 is supplied through the NAND gate N1 to the clock terminal $\overline{C}$ of flip-flop F2. The output terminals Q·$\overline{Q}$ of flip-flop F2 produce signals to the clock terminals C,$\overline{C}$ of the flip-flop F3. The signal of the output terminal Q of flip-flop F3 and the signal of the output terminal Q of the flip-flop F5 are combined through NOR gate NOR2, inputted as a control signal into the flip-flop F3. The flip-flop F4 is cascaded with the flip-flop F3. The signals of the output terminals $\overline{Q},\overline{Q}$ of flip-flops F3 and F4 are combined through NOR gate NOR3, inputted into the flip-flop F5 whose clock terminals $\overline{C}$,C respectively receive the signal of the output terminal Q of the flip-flop F2 and the inverse thereof. The signals of the output terminals Q of flip-flops F2-F5 are respectively inverted through the inverters I2-I5 and are applied to the first decoding and driving means 40.

A tens digit counter 30B similarly comprises flip-flops F6-F9, NOR gates NOR4, NOR5, and inverters I6-I9 so as to count the carry signal produced from the units digit counter 30A. A hundreds digit counter 30C comprises a flip-flop F10 for receiving as the clock pulse the carry signal provided from the tens digit counter 30B, and an inverter I10 for inverting the output signal of the flip-flop F10 applied to decoding and driving portion 40C.

The output signals of the counters 30A, 30B, 30C are decoded by the first decoding and driving circuit 40 to drive the sphygmus numbers display 50.

The first counting circuitry 30 is reset by the pulse outputted from reset pulse generating means 100.

Figure 3:
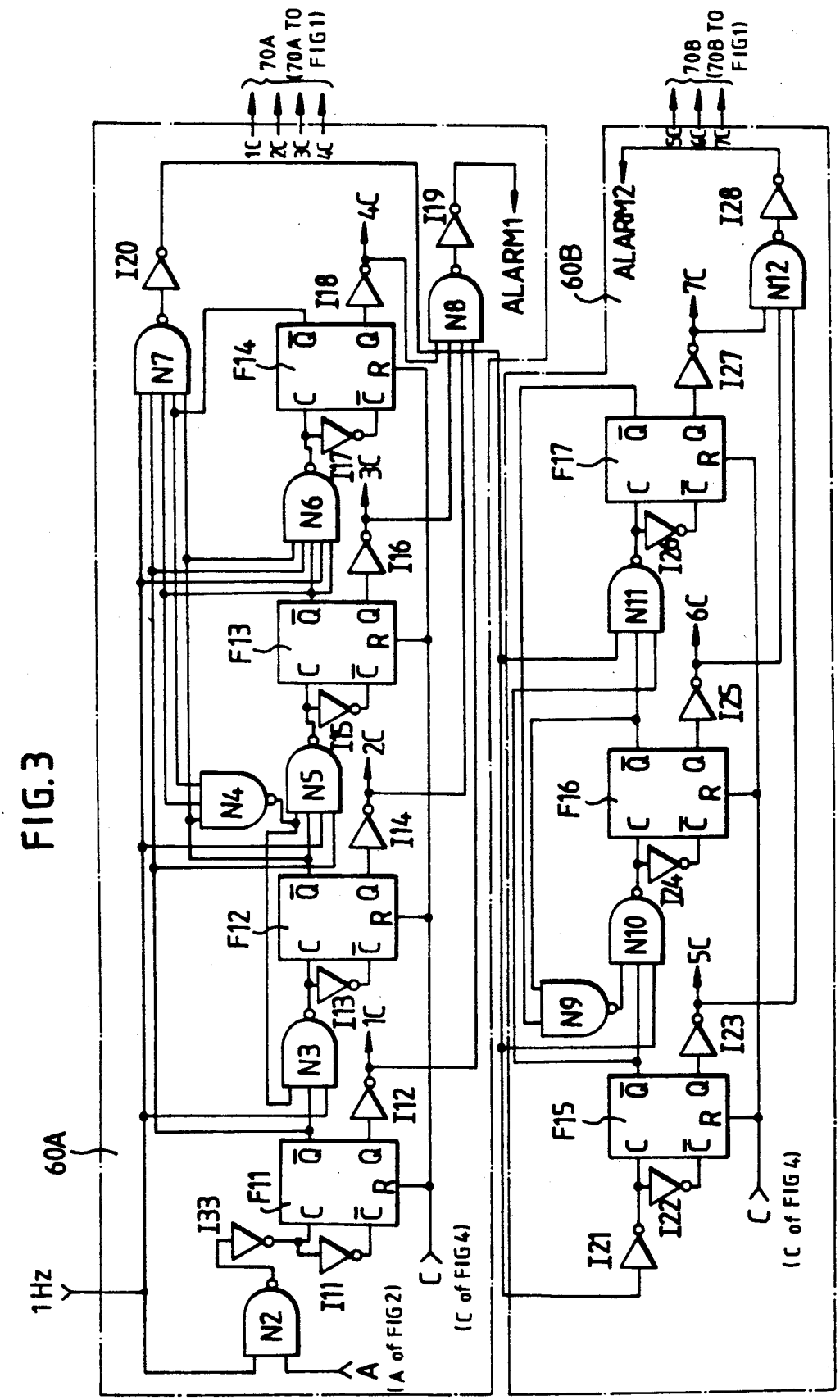
FIG. 3 is a detailed circuit diagram for illustrating second counting circuitry of FIG. 1.

Referring to FIG. 3, the second counting circuitry 60 comprises an units digit counter 60A and a tens digit counter 60B to count down during a predetermined time (for example, 60 seconds) when the pulse check mode is selected by the mode selecting means 20. The units digit counter 60A comprises NAND gates N2-N8, flip-flops F11-F14, and inverters I11-I20, I33. The NAND gate N2 gates 1 Hz signal according to the 1 Hz signal "A" outputted from the terminal Q of the flip-flop F1 in the mode selecting means 20. The output signal of NAND gate N2 is inverted by inverter I33, then delivered to clock terminal C of flip-flop F11 whose clock terminal $\overline{C}$ receives output signal of the NAND gate N2 through the two inverters I33 and I11 connected in series. The signals of output terminal $\overline{Q}$ of flip-flops F12-F14 are inputted into NAND gate N4 whose output signal and the signal of the output terminal $\overline{Q}$ are combined by NAND gate N3. The clock terminals $\overline{C}$,C of flip-flop F12 are connected to the inverted output signal of NAND gate N3 and output signal of NAND gate N3, respectively. The output signal of NAND gate N4 and the signals of output terminals $\overline{Q}$ of flip-flops F11 and F12 are inputted into NAND gate N5, whose output signal is in turn inputted into clock terminals of flip-flop F13. The signals of output terminals $\overline{Q}$ of the flip-flops F11-F13 are combined by NAND gate N6, whose output signal is inputted into clock terminals of the flip-flop F14. The signals of output terminals $\overline{Q}$ of flip-flop F11-F14 are combined by NAND gate N7, whose output signal is inverted by inverter I20. The signals of output terminals $\overline{Q}$ of flip-flops F11-F14 are respectively inverted by inverters I12, I14, I16, I18, whose output signals are combined by NAND gate N8, whose output signal is in turn inverted by inverter I19.

The tens digit counter 60B comprises flip-flops F15-F17, inverters I21-I27, and NAND gates N9-N12, counting down for the down carry signal supplied from the units digit counter 60A.

Figure 4:
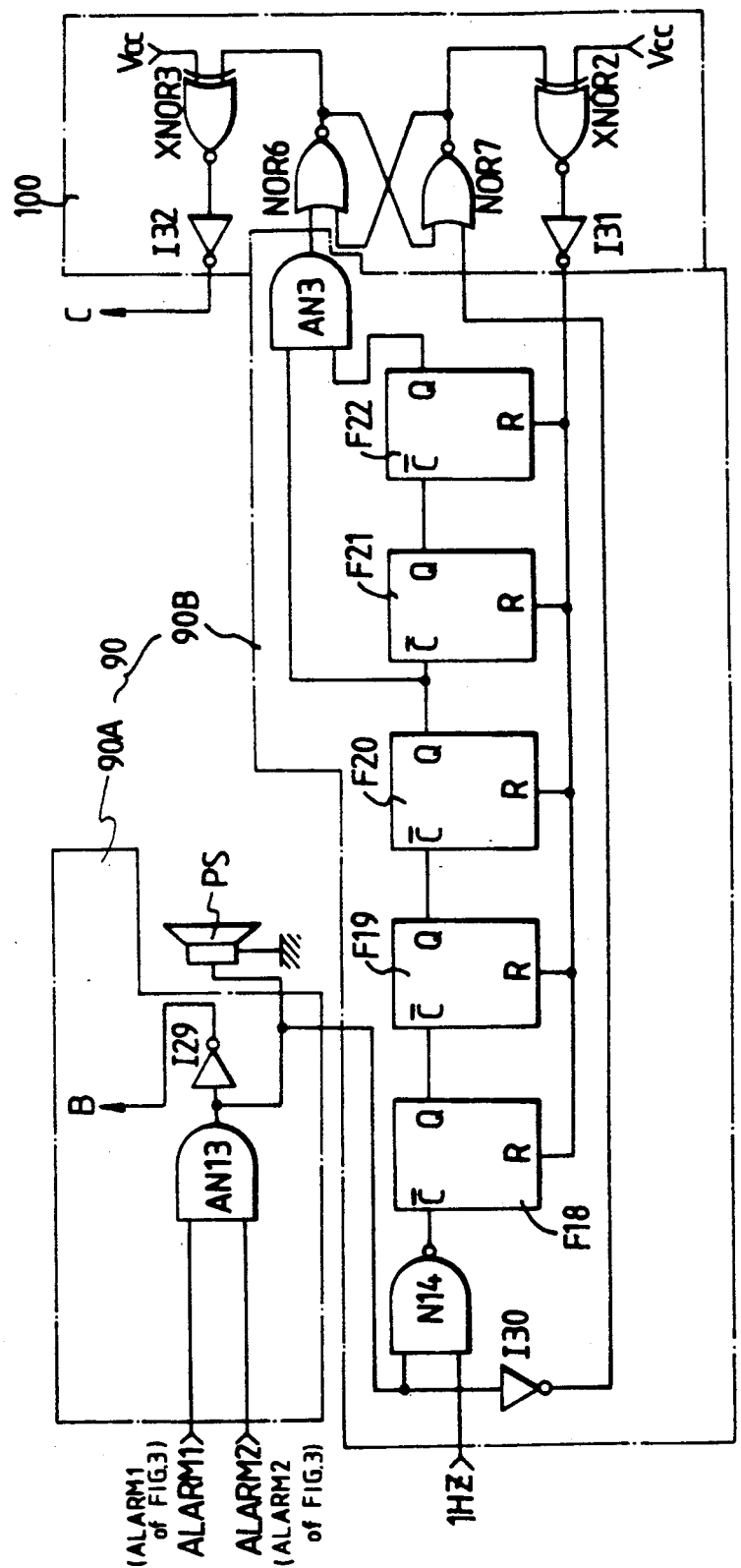
FIG. 4 is a detailed circuit diagram for illustrating alarm means and reset pulse generating means shown in FIG. 1.

Referring to FIG. 4, alarm means 90 comprises piezoelectric speaker driver 90A and alarm time setting means 90B. The piezoelectric speaker driver 90A comprises AND gate AN13 for combining alarm signals ALARM1 and ALARM2 derived respectively from the units digit counter 60A and the tens digit counter 60B; piezoelectric speaker PS for receiving the output signal of the AND gate AN13; and inverter I29 for inverting the output signal of AND gate AN13 delivered to the gate N1 of the first counting circuitry 30. The alarm time setting means 90B includes NAND gate N14 for gating 1 Hz signal according to the output signal of AND gate AN13. It further includes flip-flop F18 for receiving the output signal of NAND gate N14 as the clock pulse. Flip-flops F19-F22 are cascaded to the flip-flop F18, and AND gate AN3 for combining the output signals of flip-flops F20 and F22.

The reset pulse generating means 100 comprises RS type flip-flop consisting of NOR gates NOR6 and NOR7 to latch according to the output signal of the AND gate AN3 and the output signal of the inverter I30. Exclusive NOR gate XNOR2 and inverter I31 reset flip-flops F18-F22 according to the latching of the RS type flip-flop, and exclusive NOR gate XNOR3 and inverter I32 reset the first and second counting circuitries 30 and 60.

In operation, the inventive digital wristwatch with the function of a sphygmometers displays the instant time on the sphygmus numbers display 50 and pulse check time display 80 when toggle switch SW of mode selecting means 20 is in time check mode in FIG. 2.

When toggle switch SW of mode selecting means 20 is displaced to pulse check mode in order to check the user's sphygmus rate, the output signal of exclusive NOR gate XNOR1 is changed to low state from the high state, so that output signal of flip-flop F1 becomes high state.

The electric pulses derived from the sphygmus sensor 10 are inputted into NAND gate N1, whose output signal is delivered to clock terminal C of flip-flop F2 of units digit counter 30A of first counting circuitry 30 in the original state. If output signal of NAND gate N1 is counted by flip-flops F2-F5 to produce a signal of binary number 0101, the carry signal would apply to tens digit counter 30B, and data derived from flip-flops F2-F5 would be delivered to decoding and driving part 40A. The carry signal derived from units digit counter 30A of first counting circuitry 30 is counted by tens digit counter 30B, whose output signal is delivered to decoding and driving part 40B. The hundreds digit counter 30C comprises a latch flip-flop F10 to count the carry signal derived outputted from the tens digit counter 30B, sending the resultant data to decoding and driving part 40C. Accordingly, the user's sphygmus number would be is displayed on the sphygmus numbers display 50.

When the pulse check mode is selected by mode selecting means 20, the high signal outputted from flip-flop F1 is applied to NAND gate N2 of the units digit counter 60A of second counting circuitry 60 shown in FIG. 3. Then, NAND gate N2 outputs 1 Hz signal inputted as clock pulse into flip-flop F11, so that data $1010_2$ outputted from output terminals Q of flip-flops F11-F14 of units digit counter 60A is counted down.

The output signals of flip-flops F11-F14 of units digit counter 60A are inverted, combined by NAND gate N8, and again inverted by inverter I19, whose output is delivered to alarm means 90. The data from output terminals $\overline{Q}$ of flip-flops F11-F14 of units digit counter 60A is combined by NAND gate N7, whose output signal (carry signal) is applied to clock terminals of tens digit counter 60B. If carry signal is applied to clock terminal of flip-flop F15 of tens digit counter 60B, the output terminal Q of flip-flop F15 produces the high signal, and the remaining two flip-flops F16, F17 produce low signals, so that data supplied to decoding and driving means 70 is inverted by inverters I23, I25, I27 to give the inverted state $011_2$, thereby displaying a decimal number "6" on tens displaying portion of pulse check time display 80. Here, the tens digit counter 60B initially displays "6" which refers to pulse check time of 60 seconds. Of course, the pulse check time may be varied as desired.

The data produced from output terminals Q of flip-flops F15-F17 of tens digit counter 60B are inverted, and combined by NAND gate N12, whose output signal is inverted by inverter I28, delivered to alarm part 90A.

When units digit counter 60A and tens digit counter 60B of the second counting circuitry 60 complete the down-count operation, AND gate AN13 of alarm part 90A shown in FIG. 4 outputs high state signal. The high state signal is inverted by inverter I29 to produce the low state signal inputted into NAND gate N1 shown in FIG. 2. Thus, the output of NAND gate N1 becomes low regardless of the output of sphygmus sensor 10, thereby disabling the first counting circuitry 30.

Referring to FIG. 4, when output of AND gate AN13 becomes low, the piezoelectric speaker PS receives high signal, thereby generating a tone signal to inform the user of completion of pulse check.

The time during which the piezoelectric speaker PS generates the tone signal is controlled by the alarming time setting means 90B. Namely, if high signal is applied to one input terminal of NAND gate N14 of alarm time setting means 90B, the output of NAND gate N14 becomes inverted 1 Hz which is then signal applied to the clock terminal of flip-flop F18. Thus, when output signals of flip-flops F20, F22 are combined by AND gate AN3, and the output of AND gate AN3 is in high state with the alarm time setting means 90B setting the control time at 20 seconds, the latch circuit consisting of NOR gates NOR6, NOR7 of reset pulse generating means 100 works to initialize the flip-flops F18-F22 of alarm time setting means 90B through exclusive NOR gate XNOR2 and inverter I31 as well as supplying exclusive NOR gate XNOR3 with high level signal ALARM3, thereby resetting first and second counting circuitries 30 and 60.

Thus, if the user is to check again his pulse, it suffices to displace the toggle switch SW of mode selecting means 20 to pulse check mode in order to repeat the pulse checking steps described above.

The inventive digital wristwatch with the function of a sphygmometer as described above enables the user to conveniently check his sphygmus numbers, thereby helping manage his health.

What is claimed is:

1. In a digital wristwatch for registering time and having hours, minutes and seconds display sections, and for measuring user's sphygmus by a sphygmometer, said sphygmometer comprising:

a sphygmus sensor means for sensing sphygmus of a human body;

mode selecting means for selecting a time record mode and a pulse check mode;

first counting means for counting the number of electrical pulses derived from said sphygmus sensor means when said pulse check mode is selected by said mode selecting means;

second counting means for counting a predetermined pulse check time when the pulse check mode is selected by said mode selecting means;

alarm means for generating an alarm signal for a predetermined time and for disabling said first counting means from receiving said electrical pulses corresponding to said sphygmus, when said predetermined pulse check time has been counted by said second counting means;

reset pulse generating means for resetting said first counting means, said second counting means and said alarm means when generation of said alarm signal by said alarm means for said predetermined time is completed; and display means having decoder and driving means for displaying time and pulse information via said decoder and driving means, said display means displaying output of said first counting means on said hours and minutes display sections of said digital wrist watch, when said pulse check mode is selected, and said display means displaying output of said second counting means on seconds display section of said digital wrist watch, when said pulse check mode is selected.

2. The invention as claimed in claim 1, wherein said first counting means further comprises gating means for blocking said electrical pulses supplied from said sphygmus sensor means when said predetermined pulse check time is ended by said second counting means.

3. The invention as claimed in claim 1, wherein said second counting means counts down during said predetermined pulse check time.

* * * * *